United States Patent [19]
Castro et al.

[11] Patent Number: 5,797,959
[45] Date of Patent: Aug. 25, 1998

[54] SURGICAL APPARATUS WITH ARTICULATING JAW STRUCTURE

[75] Inventors: Salvatore Castro, Seymour; Richard A. McGarry, Norwalk, both of Conn.

[73] Assignee: United States Surgical Corporation, Norwalk, Conn.

[21] Appl. No.: 910,767

[22] Filed: Aug. 13, 1997

Related U.S. Application Data

[63] Continuation of Ser. No. 531,990, Sep. 21, 1995, abandoned.

[51] Int. Cl.$^6$ .................................................. A61B 17/28
[52] U.S. Cl. .................................................. 606/207
[58] Field of Search ........................ 606/205, 206, 606/207, 210

[56] References Cited

U.S. PATENT DOCUMENTS

| | | |
|---|---|---|
| 424,178 | 3/1890 | Chisholm . |
| 1,127,948 | 2/1915 | Wappler . |

(List continued on next page.)

FOREIGN PATENT DOCUMENTS

| | | |
|---|---|---|
| 0165472 | 12/1985 | European Pat. Off. . |
| 0412282 | 2/1991 | European Pat. Off. . |
| 0449663 | 10/1991 | European Pat. Off. . |
| 0484671 | 5/1992 | European Pat. Off. . |
| 592243 | 4/1994 | European Pat. Off. . |
| 621009 | 10/1994 | European Pat. Off. . |
| 2469912 | 11/1979 | France . |
| 2737014 | 3/1979 | Germany . |
| 3303335 | 8/1984 | Germany . |
| 8535164 | 4/1986 | Germany . |
| 8711051 | 2/1988 | Germany . |
| 8808285 | 9/1988 | Germany . |
| 9007356 | 6/1991 | Germany . |
| 9109097 | 10/1991 | Germany . |
| 9300161 | 4/1993 | Germany . |
| 990220 | 1/1893 | Russian Federation . |
| 519190 | 6/1976 | Russian Federation . |
| 980703 | 12/1982 | Russian Federation . |

OTHER PUBLICATIONS

"Surgical Instruments—Suction and Pressure Apparatus", J. Sklar Mfg. Co., Inc., 18th edition, 1973.
Instruction Manual for Uterine Mobilizer.
Stephen L. Corson, M.D., "Two New Laparoscopic Instruments: Bipolar Sterilizing Forceps and Uterine Manipulator," Medical Instrumentation, vol. 11, No. 1, Jan.–Feb. 1977.
"Nantiicoke™ Advanced Laparoscopic/Thoracoscopic Instruments For The Next Generation of Endoscopic Surgery," Cabot Medical Corporation, Jan. 1992.
"Advanced Laparoscopy", Snowden–Pencer, Apr. 1992.
"Manual Instruments", Cooper Endoscopy, Oct. 1992.
Optik Incorporated, *Surgical Products*, p. 33, Jun. 1992 edition.

*Primary Examiner*—Michael H. Thaler

[57] ABSTRACT

A surgical apparatus is provided which includes a handle portion and an elongated body portion extending distally from the handle portion and defining a longitudinal axis. A tool assembly is operatively associated with a distal end portion of the body portion and includes a first jaw assembly having a proximal jaw portion and a distal jaw portion and a second jaw assembly having a proximal jaw portion and a distal jaw portion. The distal and proximal jaw portions of each jaw assembly are pivotably connected to one another and are movable between first and second articulated positions. A jaw actuation mechanism is provided including an actuation member and having first and second cooperating actuating legs. Each leg is operatively connected to a respective distal portion of the first and second jaw assemblies to effectuate simultaneous pivotable movement of the distal jaw portions relative to the proximal jaw portions of the tool assembly. A jaw control mechanism operatively connects the handle portion and the tool assembly and is configured to effect movement of the tool assembly between an open position and a closed position.

29 Claims, 14 Drawing Sheets

U.S. PATENT DOCUMENTS

| | | |
|---|---|---|
| 1,620,828 | 3/1927 | Molony . |
| 1,918,889 | 7/1933 | Bacon . |
| 2,028,635 | 1/1936 | Wappler . |
| 2,109,147 | 2/1938 | Grosso . |
| 2,113,246 | 4/1938 | Wappler . |
| 2,507,710 | 5/1950 | Grosso . |
| 2,935,068 | 5/1960 | Donaldson . |
| 3,144,020 | 8/1964 | Zingale . |
| 3,435,824 | 4/1969 | Gamponia . |
| 3,516,408 | 6/1970 | Montanti . |
| 3,788,303 | 1/1974 | Hall . |
| 3,866,610 | 2/1975 | Kletschka . |
| 3,868,957 | 3/1975 | Doddington . |
| 3,877,433 | 4/1975 | Librach . |
| 3,880,166 | 4/1975 | Fogarty . |
| 3,892,228 | 7/1975 | Mitsui . |
| 3,993,076 | 11/1976 | Fogarty . |
| 4,000,743 | 1/1977 | Weaver . |
| 4,022,208 | 5/1977 | Valtchev . |
| 4,106,508 | 8/1978 | Berlin . |
| 4,243,047 | 1/1981 | Olsen . |
| 4,430,076 | 2/1984 | Harris . |
| 4,572,185 | 2/1986 | Rich . |
| 4,611,593 | 9/1986 | Fogarty et al. . |
| 4,646,751 | 3/1987 | Maslanka . |
| 4,721,116 | 1/1988 | Schintgen et al. . |
| 4,763,669 | 8/1988 | Jaeger . |
| 4,841,949 | 6/1989 | Shimizu et al. . |
| 4,872,456 | 10/1989 | Hasson . |
| 4,880,015 | 11/1989 | Nierman . |
| 4,887,612 | 12/1989 | Esser et al. . |
| 4,919,112 | 4/1990 | Siegmund . |
| 4,919,152 | 4/1990 | Ger . |
| 4,944,741 | 7/1990 | Hasson . |
| 4,950,273 | 8/1990 | Briggs . |
| 5,047,046 | 9/1991 | Bodoia . |
| 5,103,839 | 4/1992 | Shichman . |
| 5,104,377 | 4/1992 | Levine . |
| 5,106,369 | 4/1992 | Christmas . |
| 5,133,724 | 7/1992 | Wilson, Jr. et al. . |
| 5,133,727 | 7/1992 | Bales et al. . |
| 5,152,279 | 10/1992 | Wilk . |
| 5,171,256 | 12/1992 | Smith et al. . |
| 5,174,300 | 12/1992 | Bales et al. . |
| 5,176,699 | 1/1993 | Markham . |
| 5,178,133 | 1/1993 | Pena . |
| 5,192,298 | 3/1993 | Smith et al. . |
| 5,195,505 | 3/1993 | Josefsen . |
| 5,195,506 | 3/1993 | Hulfish . |
| 5,199,419 | 4/1993 | Remiszewski et al. . |
| 5,209,747 | 5/1993 | Knoepfler . |
| 5,235,966 | 8/1993 | Jamner . |
| 5,237,985 | 8/1993 | Hodgson et al. . |
| 5,245,987 | 9/1993 | Redmond et al. . |
| 5,258,004 | 11/1993 | Bales et al. . |
| 5,271,385 | 12/1993 | Bailey . |
| 5,282,826 | 2/1994 | Quadri . |
| 5,306,234 | 4/1994 | Johnson . |
| 5,350,391 | 9/1994 | Iacovelli . |
| 5,354,311 | 10/1994 | Kambin et al. . |
| 5,411,519 | 5/1995 | Tovey et al. . |
| 5,452,733 | 9/1995 | Sterman et al. . |
| 5,483,952 | 1/1996 | Aranyl . |
| 5,549,636 | 8/1996 | Li ........................................ 606/205 X |

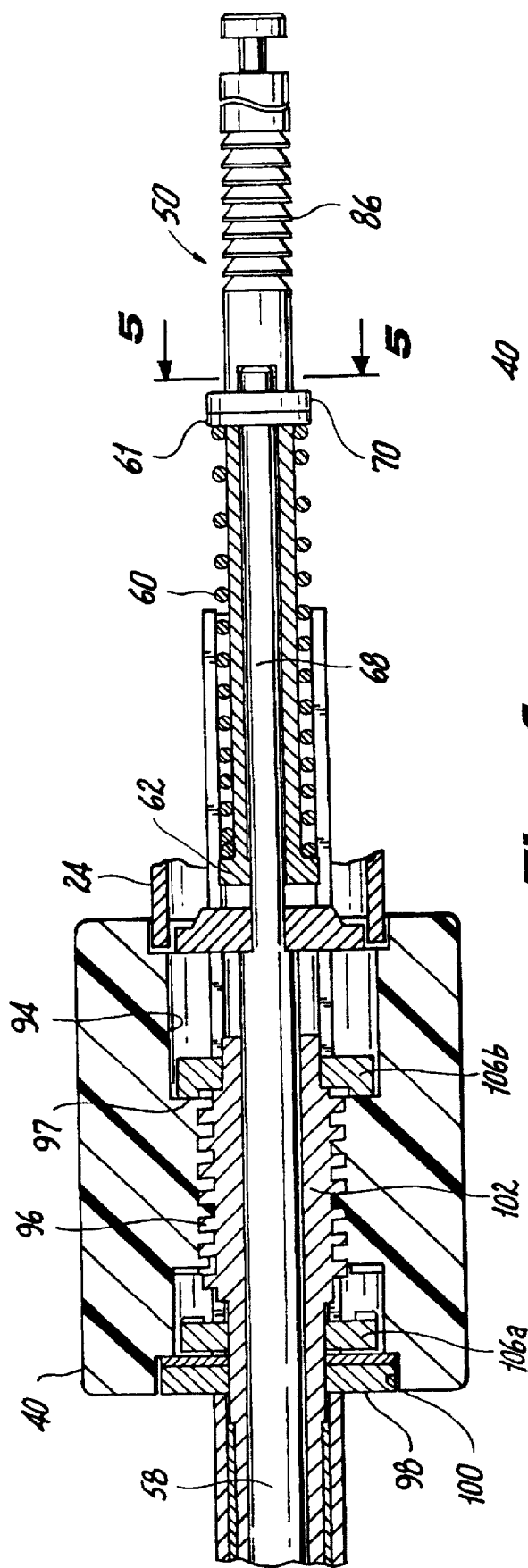
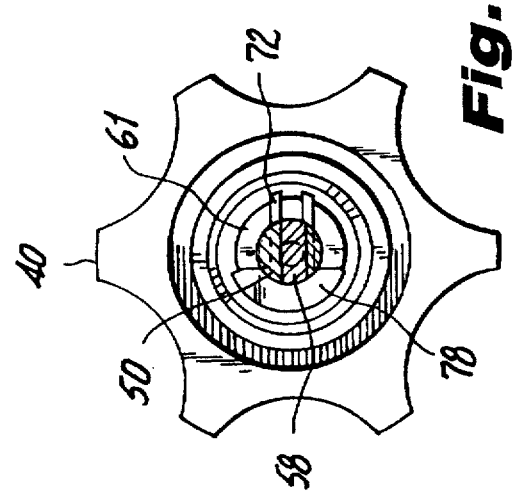
Fig. 4
Fig. 5

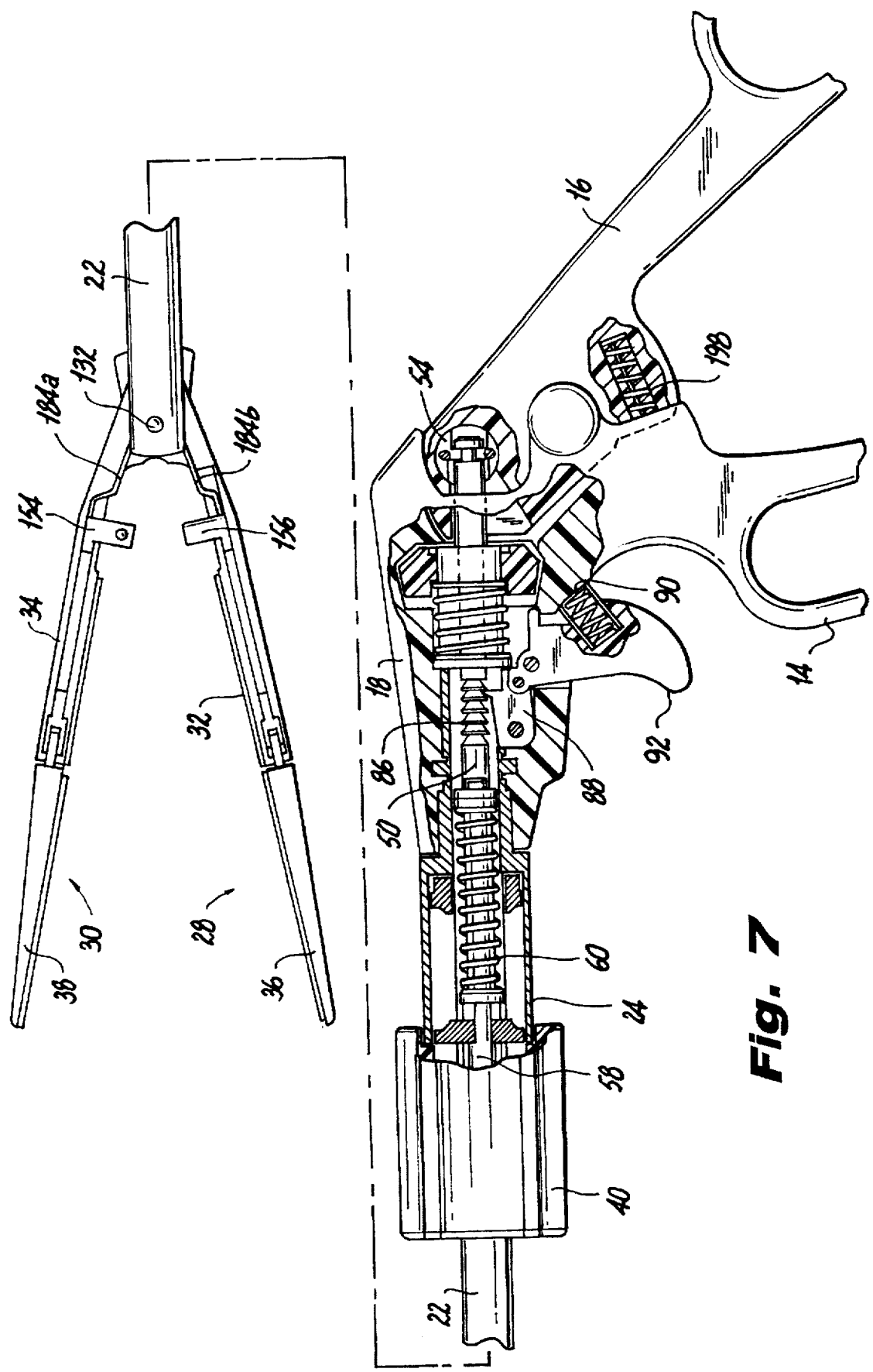

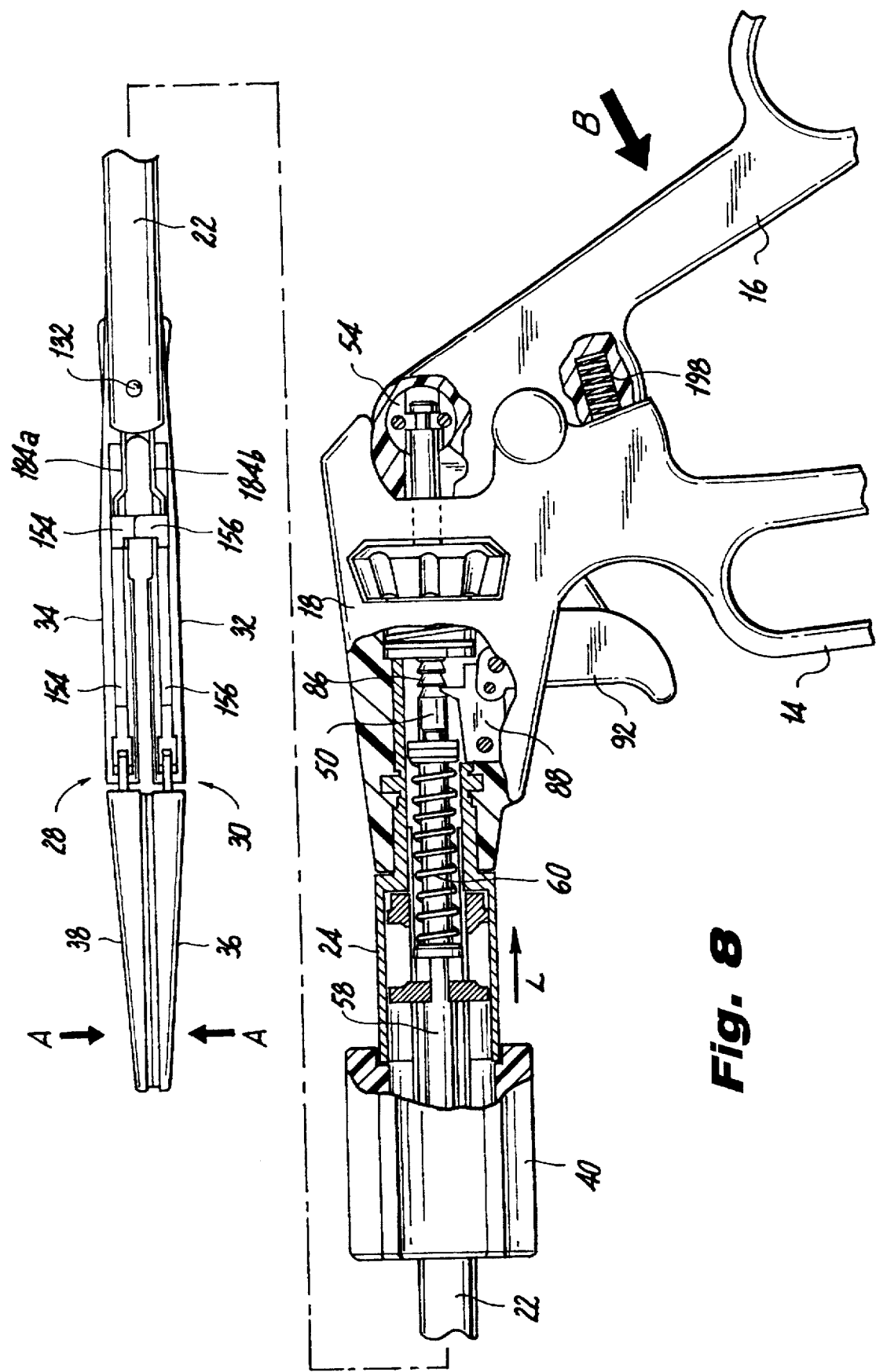

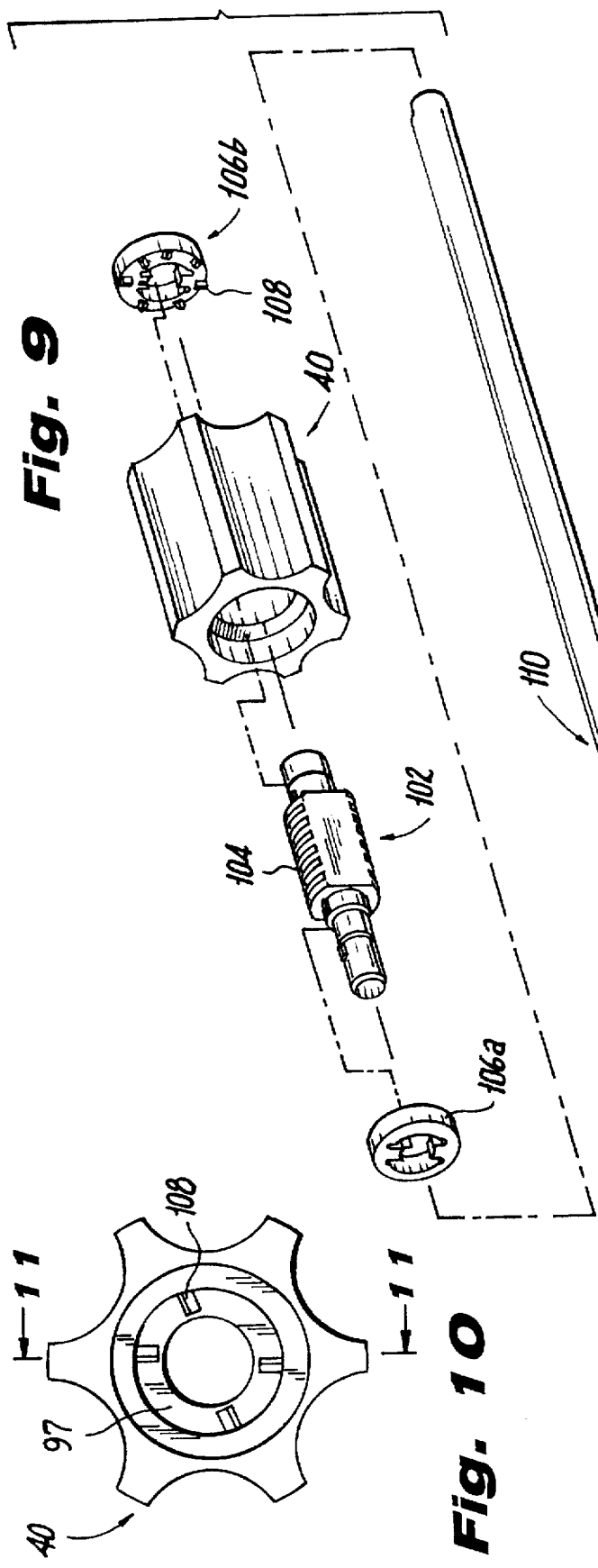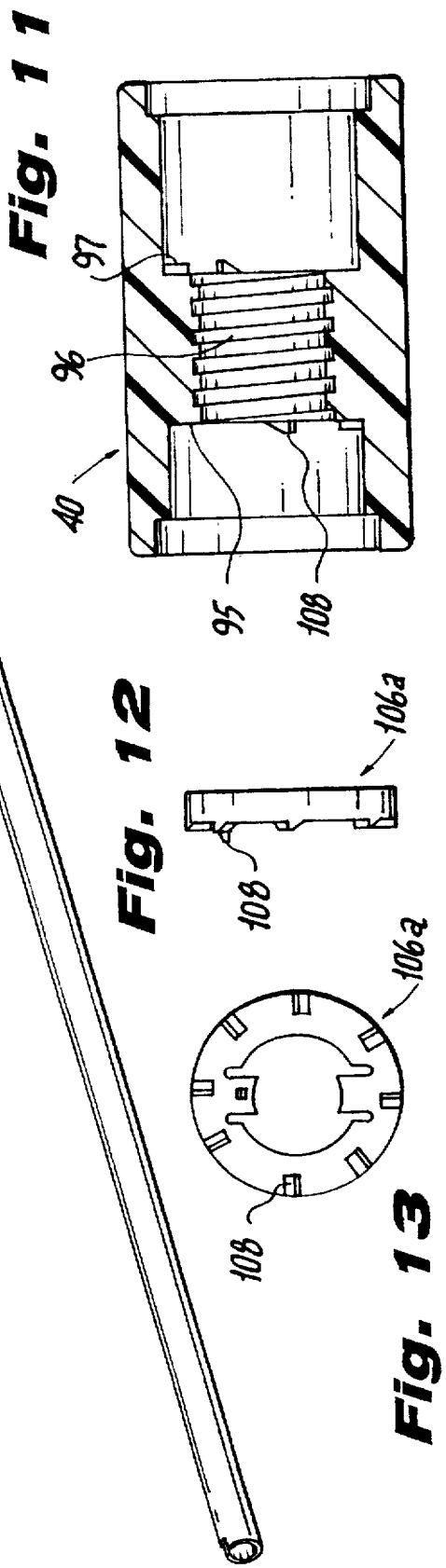

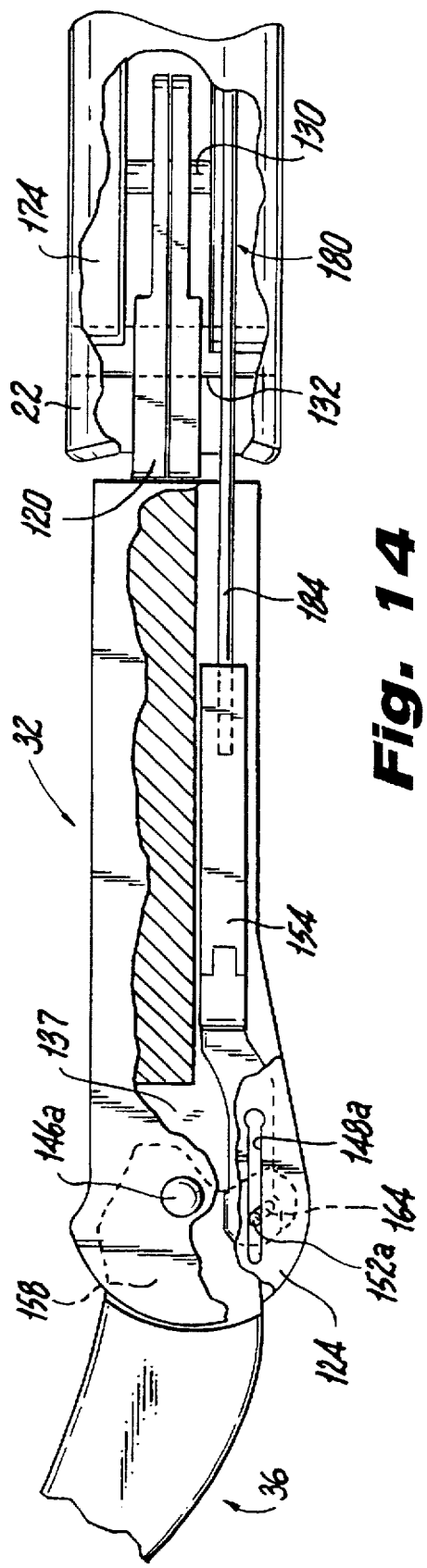
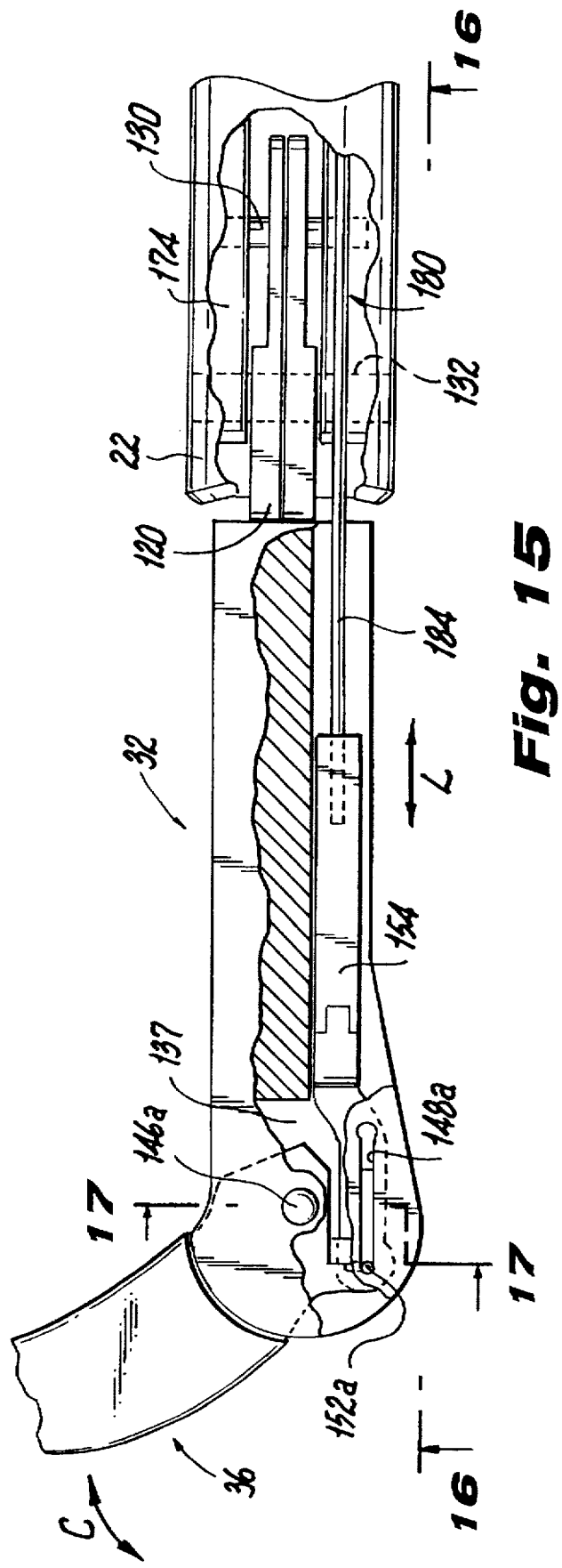
Fig. 14
Fig. 15

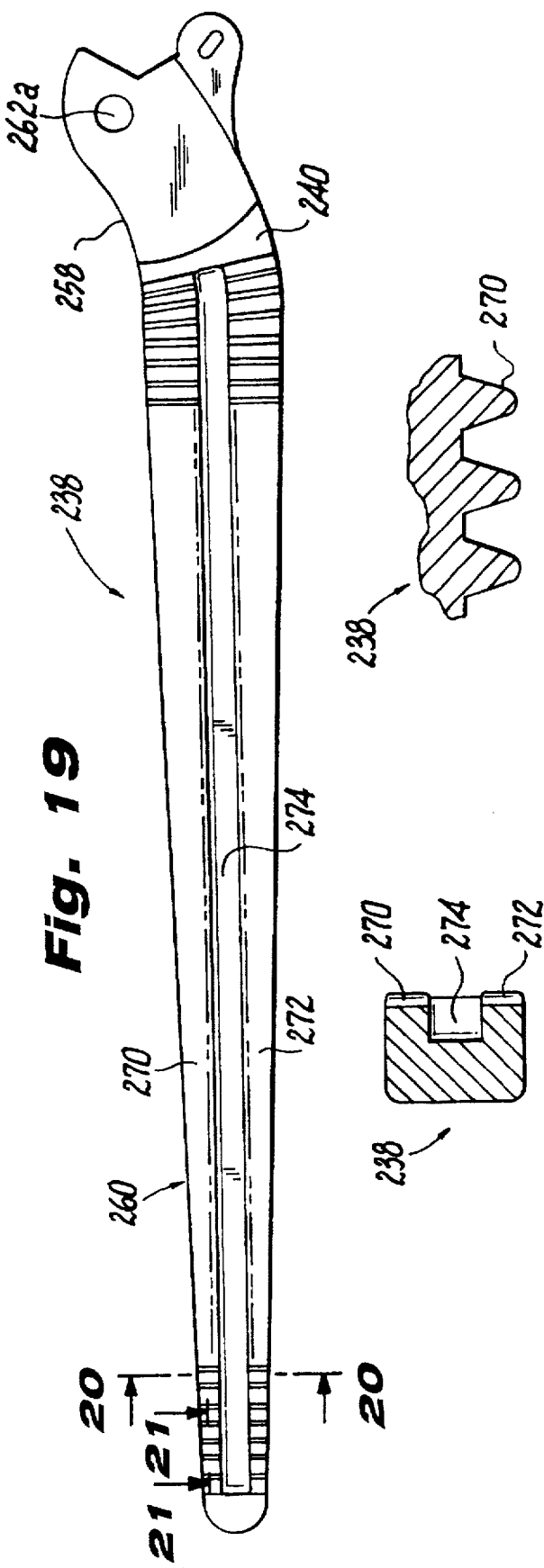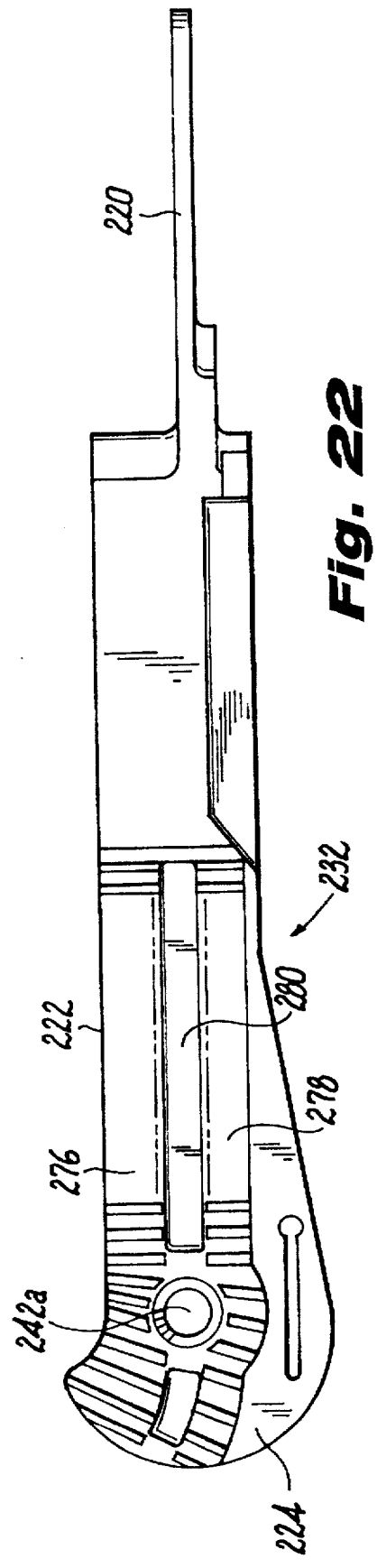

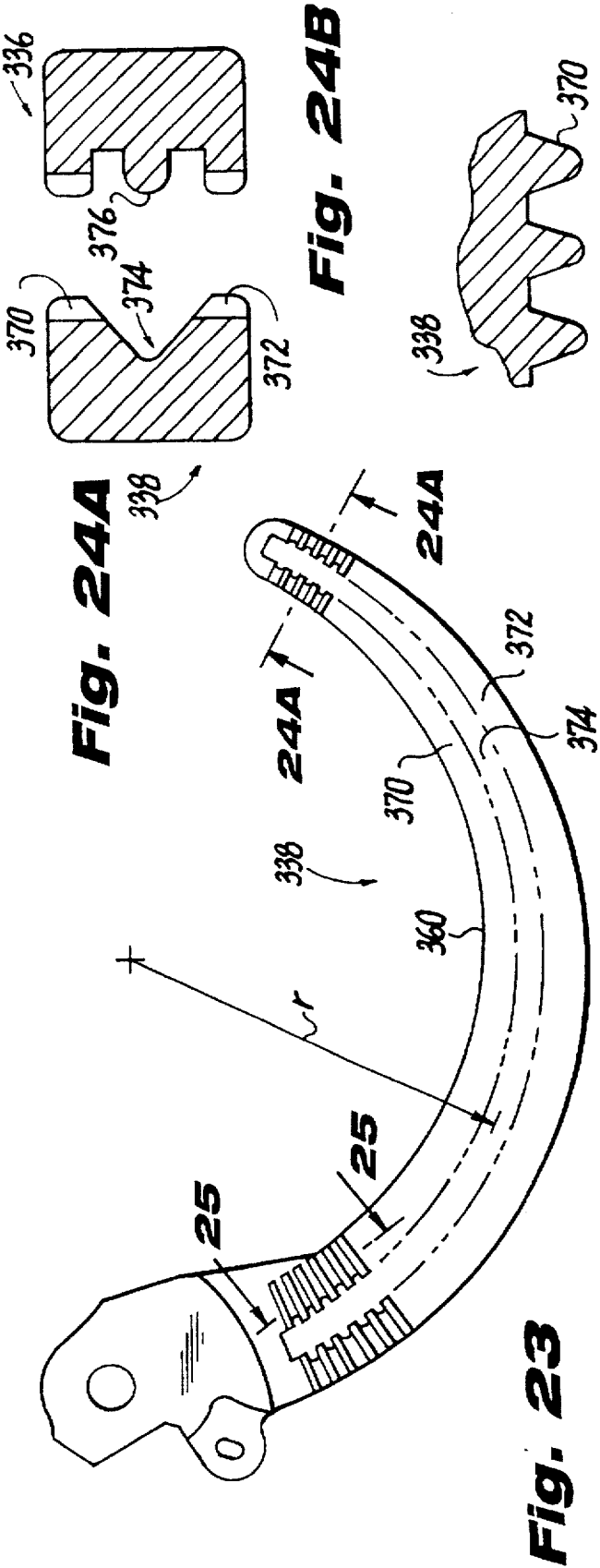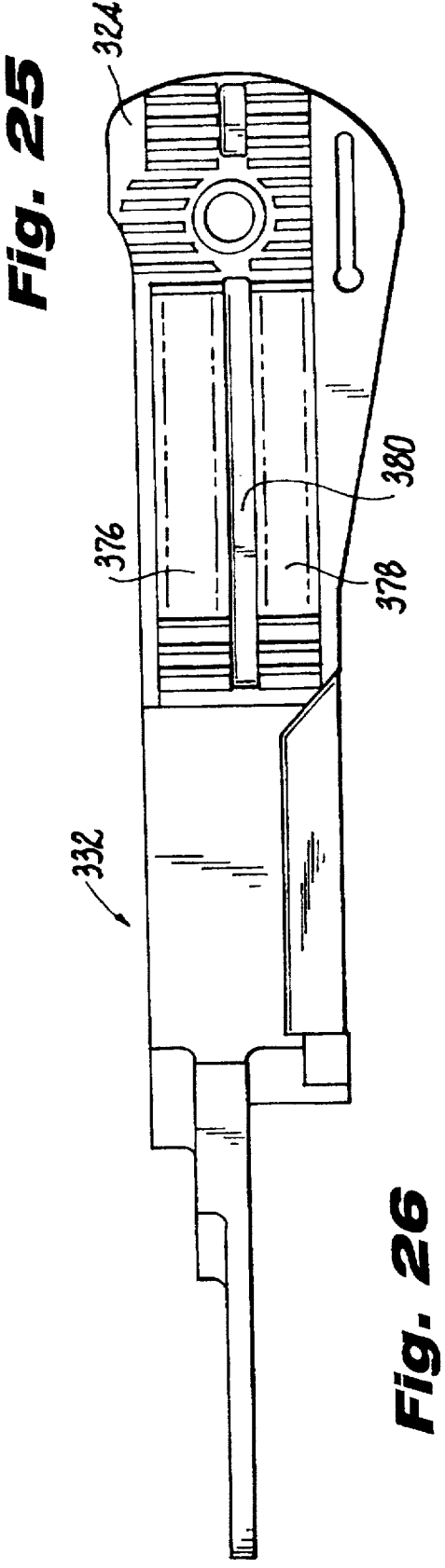

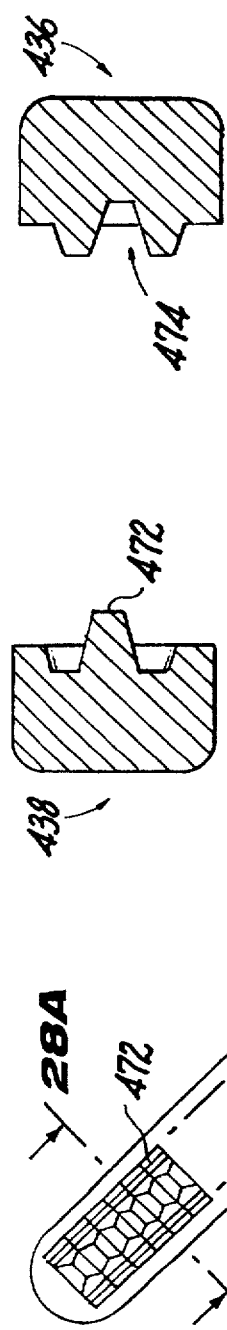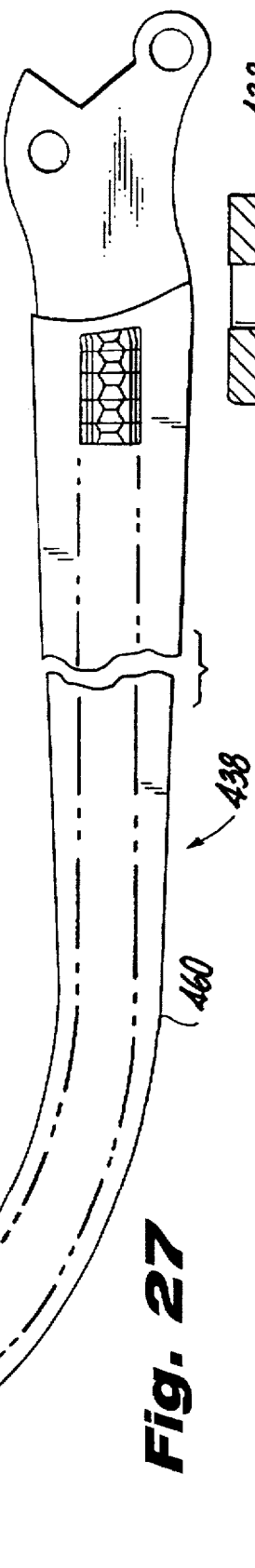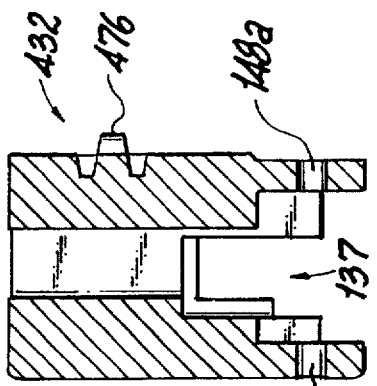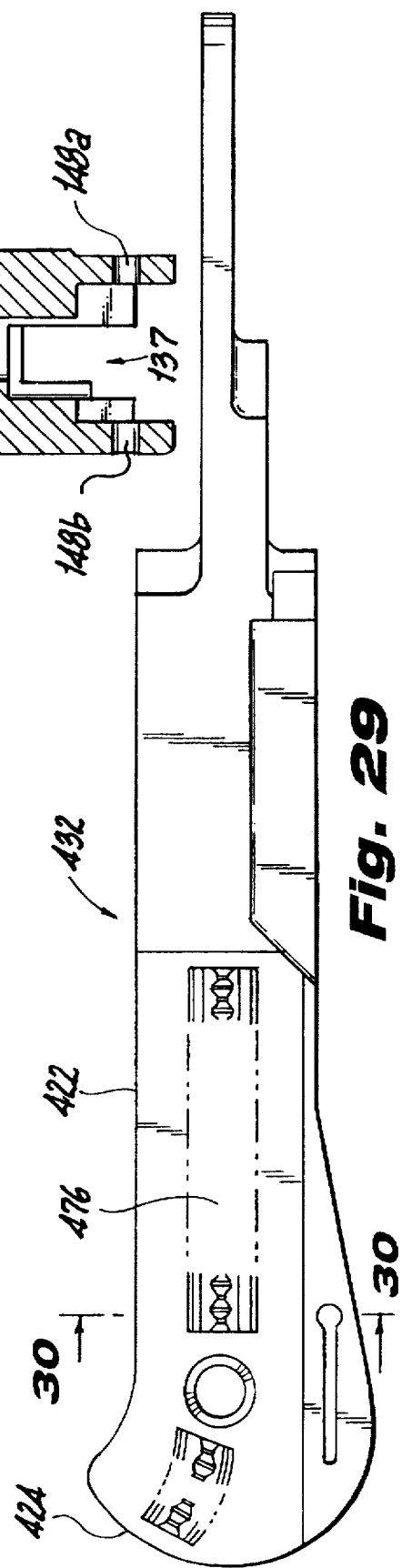

5,797,959

1

SURGICAL APPARATUS WITH ARTICULATING JAW STRUCTURE

This is a continuation of application Ser. No. 08/531,990 filed on Sep. 21, 1995 now abandoned.

BACKGROUND

1. Technical Field

The subject invention relates to surgical apparatus for performing endoscopic and laparoscopic surgical procedures, and more particularly, to surgical apparatus having articulable jaw structure.

2. Description of the Related Art

Endoscopic surgical procedures, and in particular, laparoscopic procedures in which small incisions are formed in a patient's abdominal wall to provide access for a trocar or cannula device are well known in the art. In such procedures, surgical instruments are introduced into the patient's abdominal cavity through the narrow pathway defined by the trocar or cannula.

To date, endoscopic cardiac surgical procedures have been less common since the instrumentation that is required to perform tasks such as vascular bypass procedures are poorly suited for insertion through a trocar or cannula. Moreover, many of the required tools for performing bypass surgery, such as, for example, vascular clamps, have irregular jaw structures which cannot be extended through the narrow pathway provided by the cannula. Specifically, these devices have cooperating jaws which depend either angularly or arcuately from the longitudinal axis of the instrument, making passage through a cannula virtually impossible. Consequently, there exists a need in the art for instruments having jaw configurations such as these which may be utilized in endoscopic procedures, and more particularly during endoscopic bypass surgery.

It is desirable therefore, to provide an endoscopic surgical instrument having angularly or arcuately configured jaw members adapted for insertion through a trocar or cannula device, and more particularly, to provide an instrument having articulable jaw structure adapted for insertion through a cannula device during endoscopic cardiac procedures.

SUMMARY

The subject application is directed to a surgical apparatus which includes a handle portion and an elongated body portion extending distally from the handle portion and defining a longitudinal axis. A tool assembly is operatively associated with a distal end portion of the body portion and includes a first jaw assembly having a proximal jaw portion and a distal jaw portion and a second jaw assembly having a proximal jaw portion and a distal jaw portion. The distal and proximal jaw portion of each jaw assembly are pivotably connected to one another and movable between first and second positions. A jaw mechanism is provided including a bifurcated actuation member having first and second cooperating actuating legs. Each leg extends at least partially through a respective one of the proximal portion of the first and second jaw assemblies and connects with a respective one of the distal jaw portions of the first and second jaw assemblies. Upon longitudinal translation of the actuation member, the distal jaw portions articulate with respect to the proximal jaw portions. A jaw control mechanism operatively connects the handle portion and the tool assembly and is configured to effectuate movement of the tool assembly between an open position and a closed position.

2

These and other features of the subject surgical apparatus will become more readily apparent to those skilled in the art from the following detailed description of the subject application.

BRIEF DESCRIPTION OF THE DRAWINGS

Various embodiments of the subject surgical apparatus are described herein with reference to the drawings wherein:

FIG. 4 is a side elevational view in partial cross-section of the elongated endoscopic portion of the surgical apparatus of FIG. 1;

FIG. 5 is a cross-sectional view taken along line 5—5 of FIG. 4 illustrating the endoscopic portion adjacent the interconnection of the proximal and distal control members;

FIG. 7 is a side elevational view in partial cross section of the surgical apparatus of FIG. 1 with the jaws depicted in an open position and the corresponding position of the pivoting actuation handle;

FIG. 8 is a side elevational view in partial cross-section of the surgical apparatus with the jaws depicted in a closed position and the corresponding position of the pivoting actuation handle shown with arrows illustrating the direction of movement of the parts;

FIG. 9 is an exploded perspective view of the articulation mechanism which effectuates pivotal movement of the distal jaw sections;

FIG. 10 is a front end elevational view of the articulation knob shown in FIG. 9;

FIG. 11 is a side elevational view in cross-section of the articulation knob of FIG. 9, taken along line 11—11 of FIG. 10;

FIG. 12 is a side elevational view of an end plate associated with the articulation knob of FIG. 10;

FIG. 13 is a front end view of the end plate illustrated in FIG. 12;

FIG. 14 is a side elevational view in partial cross-section of the right jaw assembly, with the distal jaw section disposed in a non-articulated position;

FIG. 15 is a side elevational view in partial cross-section of the right jaw assembly, with the distal jaw section disposed in an articulated position;

FIG. 19 is a side elevational view of one embodiment of a distal jaw portion constructed in accordance with a preferred embodiment of the subject apparatus;

FIG. 20 is a cross-sectional view of the distal jaw portion of FIG. 19, taken along line 20—20 of FIG. 19, illustrating the teeth and central channel structure;

FIG. 21 is a partial cross-sectional view of the distal jaw portion of FIG. 19, taken along line 21—21 of FIG. 19, illustrating the interdigitating teeth;

FIG. 22 is a side elevational view of the proximal jaw portion of the jaw assembly of FIG. 19;

FIG. 23 is a side elevational view of a distal jaw portion having an arcuate geometric configuration constructed in accordance with another embodiment of the subject apparatus;

FIG. 24-A is a cross-sectional view of the tissue contacting surface of the distal jaw section of FIG. 23, taken along line 24—24 of FIG. 23, illustrating the channel structure;

FIG. 24-B is a cross-sectional view of distal jaw portion corresponding to that shown in FIG. 24-A of a cooperating distal jaw portion and the tissue contacting surface thereof;

FIG. 25 is a partial cross-sectional view of the distal jaw portion of FIG. 23, taken along line 25—25 of FIG. 23, illustrating the interdigitating teeth;

FIG. 26 is a side elevational view of the proximal jaw portion of a jaw assembly of FIG. 23;

FIG. 27 is a side elevational view of the distal jaw portion constructed in accordance with another embodiment of the subject apparatus;

FIG. 28-A is a cross-sectional view of the distal jaw portion of FIG. 27, taken along line 28A—28A of FIG. 27, illustrating the tissue contacting surface thereof;

FIG. 28-B is a cross-sectional view corresponding to that shown in FIG. 28-A of a cooperating distal jaw portion and the tissue contacting surface thereof;

FIG. 29 is a side elevational view of the proximal jaw portion, constructed in accordance with a preferred embodiment of the subject apparatus; and FIG. 30 is a cross-sectional view of the proximal jaw portion of FIG. 29, taken along line 30—30 of FIG. 27, indicating the recessed portion for receiving the distal jaw portion and the articulating linkage member.

DETAILED DESCRIPTION OF PREFERRED EMBODIMENTS

Figure 1:
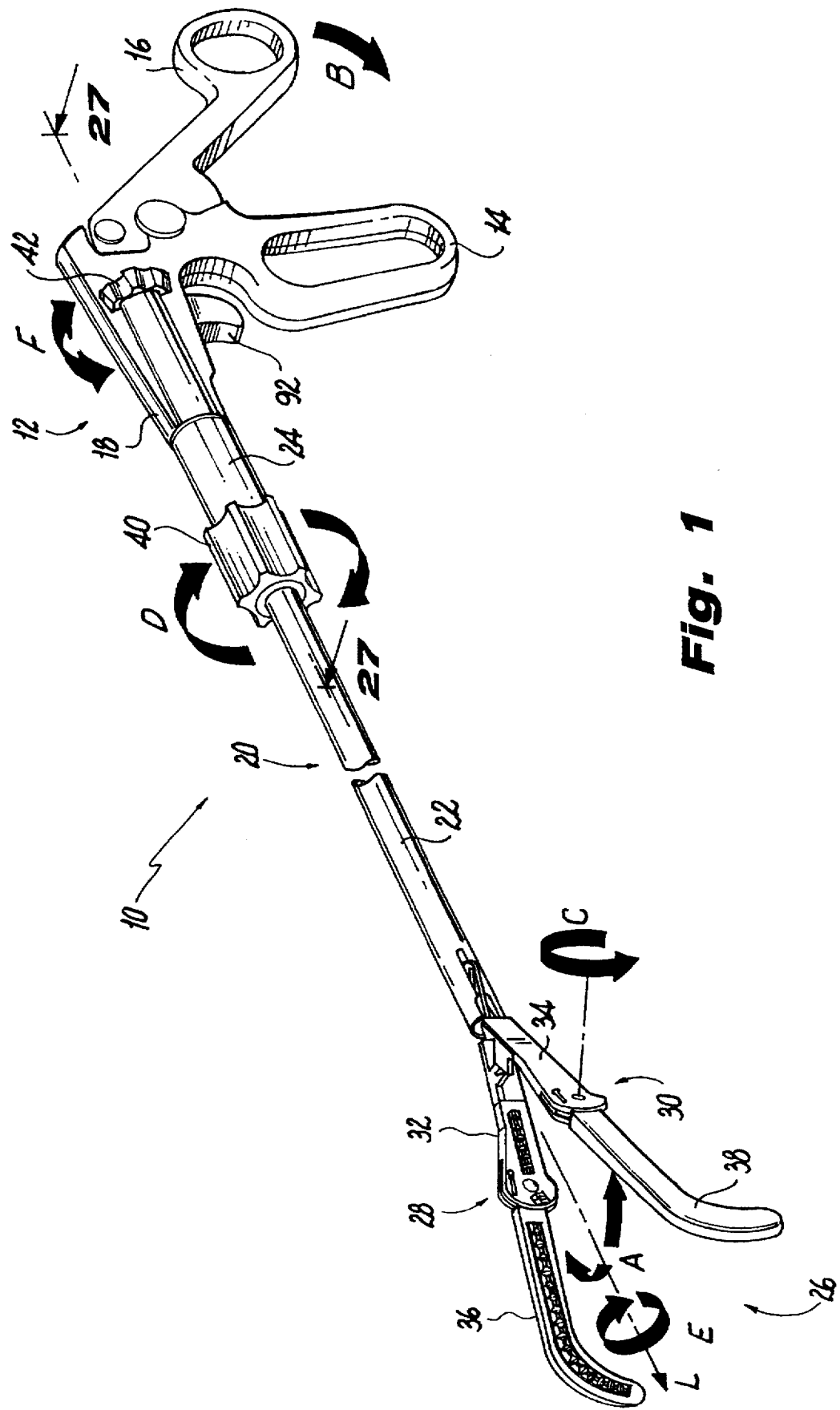
FIG. 1 is a perspective view of a surgical apparatus constructed in accordance with a preferred embodiment of the subject application.

The apparatus disclosed herein will be discussed in terms of endoscopic procedures and apparatus. However, use herein of terms such as "endoscopic" should not be construed to limit the present application to an apparatus for use only in conjunction with an endoscopic tube. In addition, it is believed that the present apparatus may find use in laparoscopic or arthroscopic surgery wherein access to the surgical site is achieved through a narrow cannula or trocar device.

In the drawings and in the description which follows, the term "proximal," as is traditional, will refer to the end of the apparatus which is closest to the operator, while the term "distal" will refer to the end which is furthest from the operator.

Referring now in detail to the drawings in which like reference numerals identify similar or identical elements, a preferred embodiment of the surgical apparatus of the subject invention is illustrated in FIG. 1, and is designated generally by reference numeral 10. Surgical apparatus 10 includes a handle assembly 12 defining a stationary handle 14, a pivoting handle 16, and a barrel portion 18. An elongated endoscopic portion extends from the barrel portion 18 of handle assembly 12 and includes elongated outer tube 22, and outer housing 24. Tool structure, specifically, in this case, vascular clamp 26, is operatively connected to a distal portion of endoscopic portion 20 and may be formed in a wide variety of configurations including graspers, dissectors, forceps, and other types of clamps.

Vascular clamp 26 includes a pair of cooperating jaw assemblies 28, 30, which open and close in a plane designated by directional arrow "A" in response to movement of pivoting handle 16 in the direction of arrow "B". Left jaw assembly 28 includes proximal jaw portion 32 and distal jaw portion 36. Right jaw assembly 30 includes proximal jaw portion 34 and distal jaw portion 38. Distal jaw portions 36, 38 are progressively articulable with respect to the proximal jaw portions 32, 34, as illustrated by arrow "C" in FIG. 1.

An articulation assembly which includes articulation knob 40 is located at a proximal portion of endoscopic portion 20 to effect relative movement of the distal jaw portions. Specifically, articulation is effectuated by rotation of articulation knob 40 in a direction indicated by arrow "D". Rotation of the clamp assembly 26 in the direction of arrow "E" about the longitudinal axis defined by endoscopic portion 20 is remotely achieved by rotation knob 42 provided at the barrel portion 18 of the handle assembly 12. The profiles and inner clamping surfaces of jaw assemblies 28, 30 may be configured as surgical procedures require. Preferred embodiments of jaw assemblies 28, 30 will be described hereinbelow.

Approximation Mechanism

Figure 2:
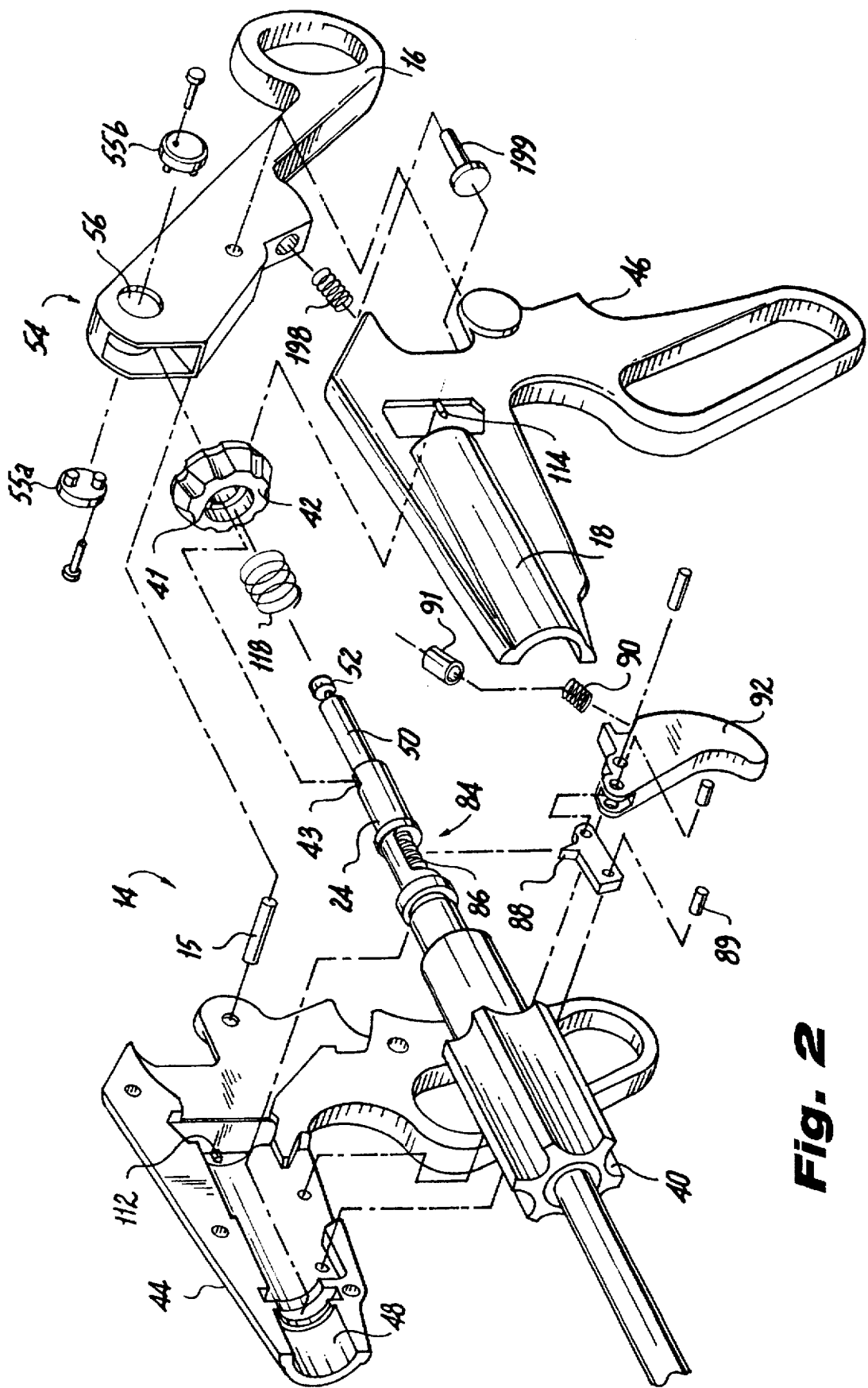
FIG. 2 is an exploded perspective view with parts separated for ease of illustration of the handle portion of the surgical apparatus of FIG. 1.

Referring to FIG. 2, handle assembly 12 of surgical apparatus 10 includes stationary handle 14, which is composed of complementary sections 44, 46. A portion of a stepped bore 48 is provided in sections 44 and 46 for accommodating various components which will be described hereinbelow. A proximal control member 50 is slidably supported within stepped bore 48. Proximal control member 50 includes a proximal head portion 52 which is retained in a universal joint assembly 54 including retaining clip portions 55a, 55b disposed within an aperture 56 formed in the pivoting handle 16 of handle assembly 12. Relative movement of pivoting handle 16 with respect to stationary handle 14 about pivot pin 15 effectuates the reciprocal longitudinal displacement of proximal control member 50, thereby progressively opening and closing jaw assemblies 28 and 30 operatively connected thereto, as will be described hereinbelow.

Surgical instrument 10 further includes an indexing mechanism to control movement of pivoting handle 16 with respect to the stationary handle 14. This permits incremental closure of jaw assemblies 28 and 30. A return spring 198 biases pivoting handle 16 to an open position corresponding to a distal position of proximal control member 50 and an open position of jaw assemblies 28 and 30 (See, FIG. 7). Proximal control member 50 is provided with a ratchet assembly having a rack 84 and a pawl 88. Rack 84 is composed of annular sloped notches 86 which permit engagement with pawl 88 independent of the angular orientation of proximal control member 50 about the longitudinal axis. Pawl 88 is supported on stationary handle 12 and pivotably interconnected to trigger 92. Pawl 88 is normally biased into engagement with rack 84 by ratchet spring 90 disposed within spring sleeve 91. Sloped notches 86 permit incremental movement of proximal control member 50 in a first longitudinal direction, while inhibiting motion in a second, opposite longitudinal direction. Preferably, sloped notches 86 are configured to permit proximal motion of control member 50 while inhibiting distal motion thereof. Consequently, pivoting handle 16 is inhibited from opening further with respect to stationary handle 14, and thus clamp assembly 26 is maintained in a desired position. A trigger 92 is provided to pivot the pawl 88 against the ratchet spring bias and out of engagement with rack 84 to permit opening of pivoting handle 16. By maintaining pressure on trigger 92, unrestricted movement of pivoting handle 16 and clamp assembly 26 is enabled.

Figure 3:
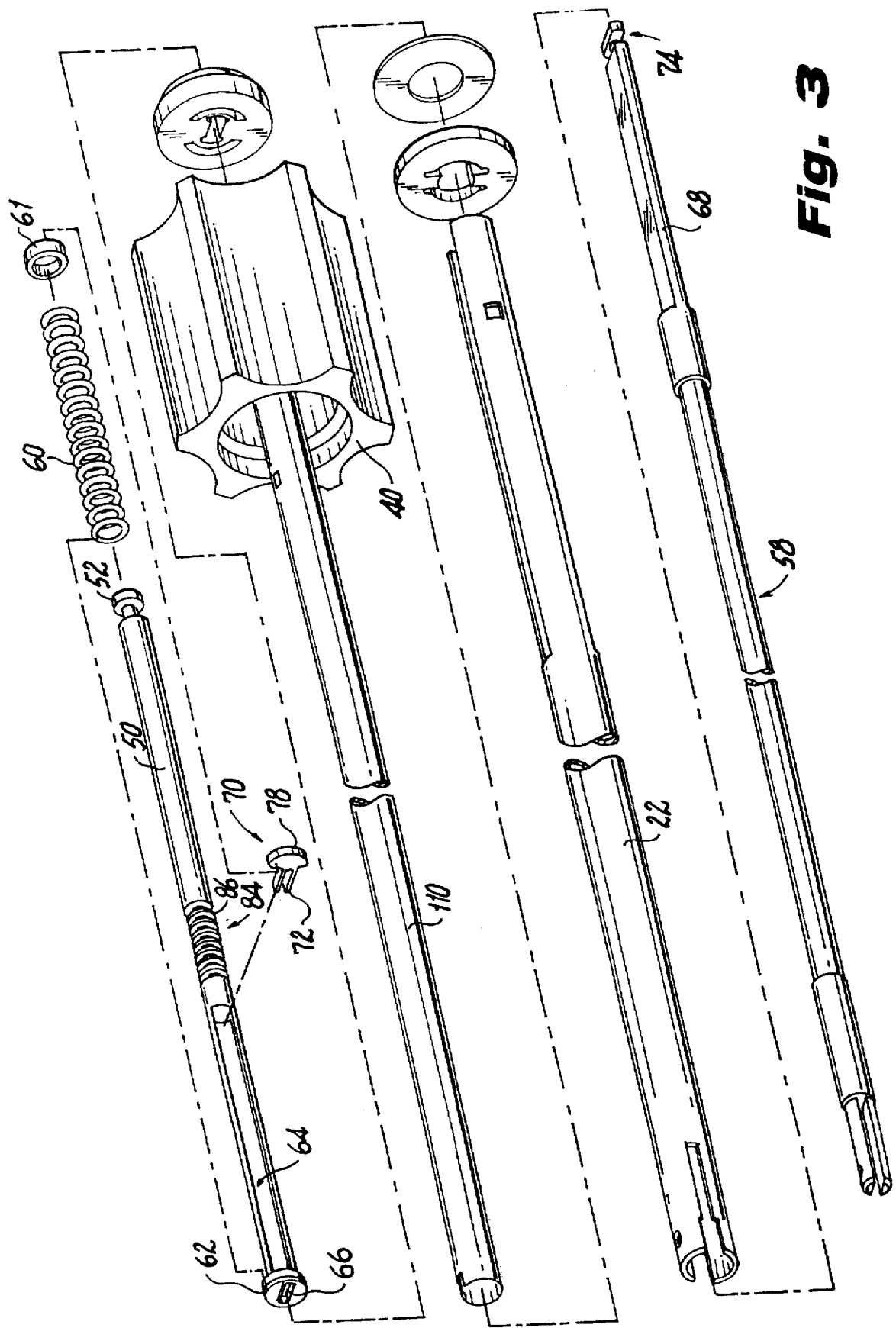
FIG. 3 is an exploded perspective view of the elongated endoscopic portion of the surgical apparatus of FIG. 1.

As illustrated in FIG. 3, proximal control member 50 is slidably connected to a distal control member 58. A longitudinal slot 64 extends axially through opposite sides of proximal member 50 at a distal portion thereof. Slot 64 terminates at distal head portion 62 and is aligned with a substantially rectangular aperture 66 extending through distal head portion 62 for receiving proximal end portion 68 of distal control member 58. A substantially rectangular cross-section of distal control member 58 is sized and configured to be inserted within aperture 66 and reciprocate longitudinally within slot 64. A retaining clip 70 is provided with a pair of prongs 72 that surround an annular notch 74 at the proximal end portion of rectangular portion 68, and fit within longitudinal slot 64, such that retaining clip 70 is fixed with respect to distal control member 58 and slides therewith in slot 64 (See, FIG. 5). An annular spacer 61 is sized to fit around the cooperating proximal control member 50 and rectangular portion 68 of distal control member 58, and is restrained from proximal movement by a bearing surface 78 of retaining clip 70.

Referring now to FIG. 4, a biasing member, such as drive spring 60, maintains proximal control member 50 in alignment with distal control member 58. Preferably, drive spring 60 is a conventional stainless steel helical spring with a distal end portion abutting an annular bearing surface on distal head portion 62 and a proximal end portion abutting the annular spacer 61. The spring characteristics of drive spring 60 are selected such that a fixed relative displacement of control members 50, 58 is generally provided. However, drive spring 60 permits some differential displacement of distal control member 58 with respect to proximal control member 50 upon encountering substantial resistance. This resilience permits the jaw assemblies 28, 30 to yield slightly when adjusted by pivoting handle 16 against a resistant structure. Alternatively, it is envisioned that jaw assemblies 28 and 30 can be actuated by a single control member replacing proximal control member 50 and distal control member 58.

Figure 6:
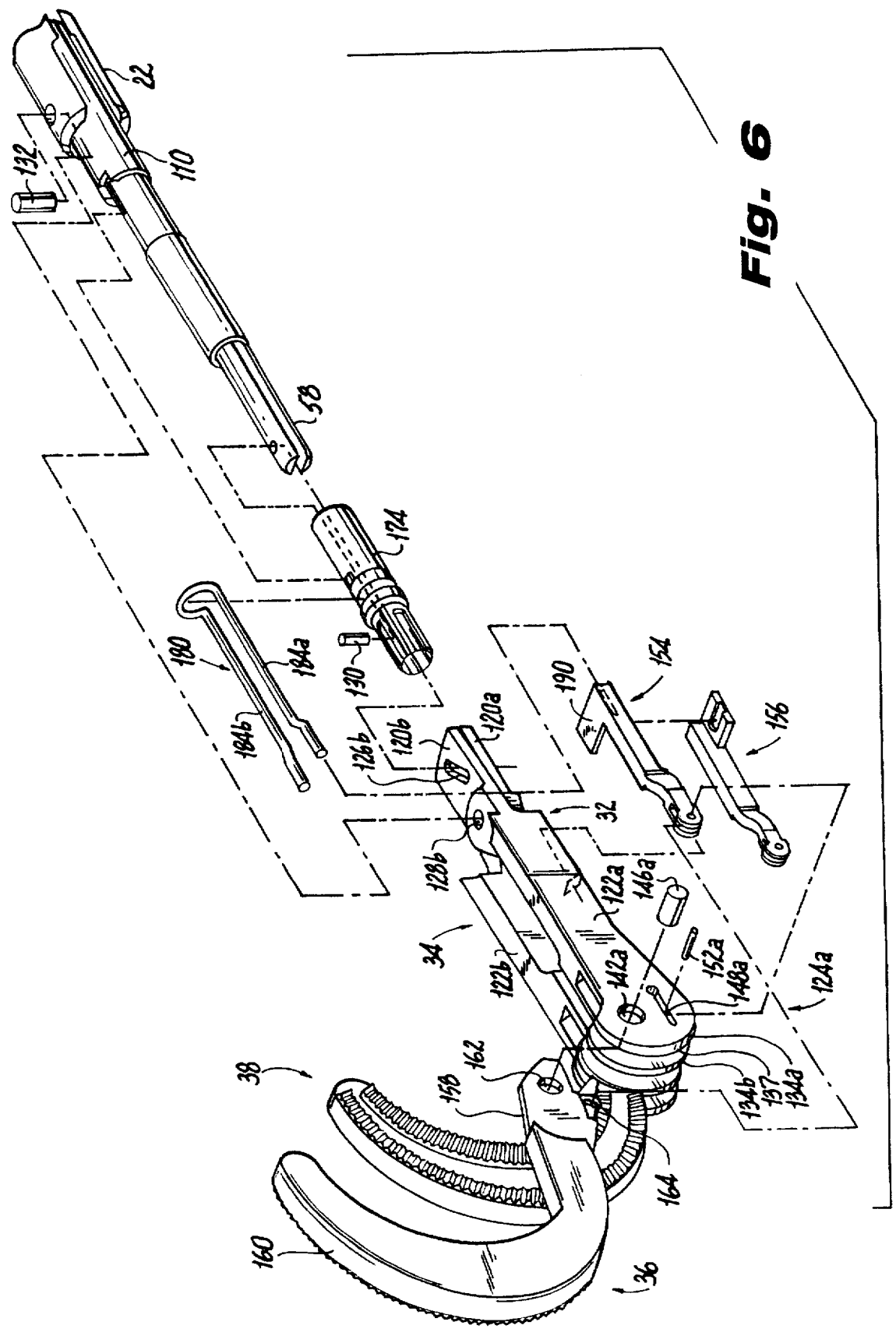
FIG. 6 is an exploded perspective view with parts separated for ease of illustration of the distal end portion of the endoscopic section and the associated tool structure.
Figure 16:
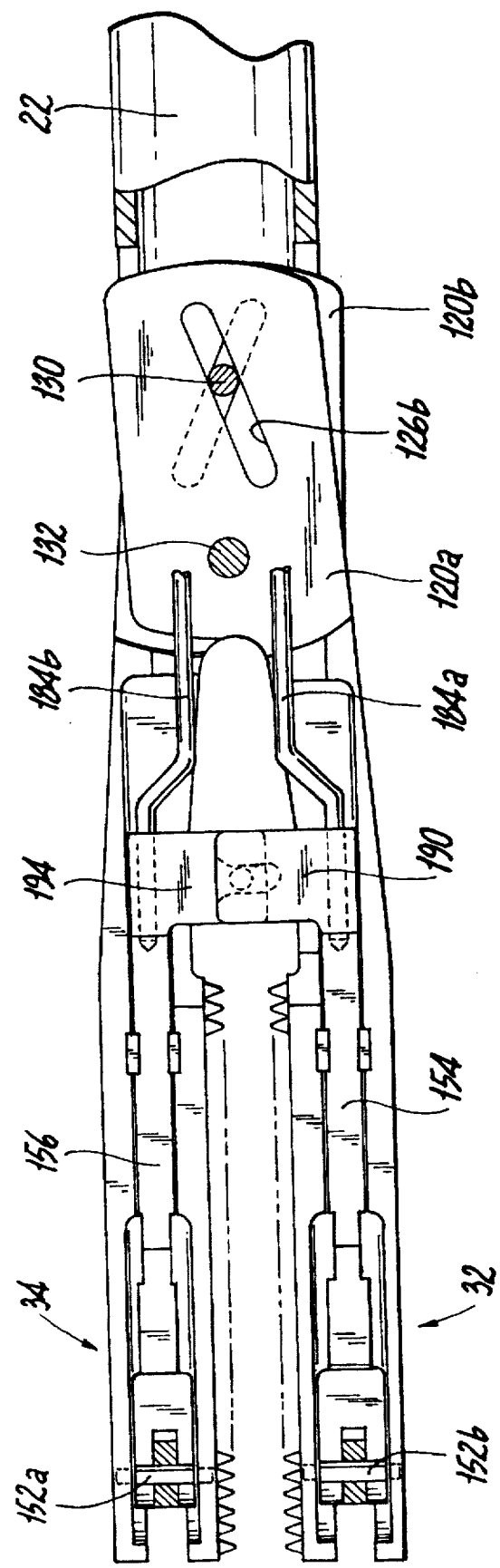
FIG. 16 is a top plan view of the proximal jaw portion and articulation linkage associated therewith with the jaw disposed in a closed position, taken along line 16—16 of FIG. 15.

Referring now to FIG. 6, the distal portion of surgical apparatus 10 will be described. As noted above, each jaw assembly includes a proximal and distal jaw portion. Proximal jaw portions 32 and 34 each include a flange portion 120a and 120b for pivotably mounting to outer tube 22, an intermediate portion 122a and 122b, and a clevis portion 124a and 124b for respectively connecting to distal jaw portions 36 and 38. Flange portions 120a and 120b are provided with an angularly disposed cam slot 126a and 126b and an adjacent pivot aperture 128a and 128b. Proximal jaw portions 32 and 34 each pivot about pivot pin 132 which is mounted at a distal end of outer tube 22. Cam slot 126a in jaw section 32 is disposed at an angle complementary to the angle at which the cam slot 126b in proximal jaw portion 34 is disposed. A cam pin 130 is mounted at the distal end of distal control member 58 and is positioned to translate within cam slots 126a and 126b. Cooperative movement of proximal jaw portions 32 and 34 is effectuated between an open position and a closed position in response to reciprocal longitudinal movement of distal control member 58.

Turning to FIGS. 7—8, approximation of jaw assemblies 28 and 30 is achieved by movement of pivoting handle 16 with respect to stationary handle 14. Referring particularly to FIG. 7, the open position of jaw assemblies 28, 30 corresponds to proximal control member 50 and distal control member 58 both being disposed in a distal position. In addition, return spring 198 is disposed between stationary handle 14 and pivoting handle 16 and guided by plunger 199 passing through the center of return spring 198 to maintain distal control member 58 in the distal position by normally biasing pivoting handle 16 in a position spaced from stationary handle 14, and pawl 88 is normally engaged with sloped notch 86 of rack 84 to inhibit distal movement of control member 50. It is also contemplated that in the distal position, with the jaws open, the pawl need not be engaged with the rack.

As illustrated in FIG. 8, in operation, progressive approximation of pivoting handle 16 with respect to stationary handle 14 in the direction of arrow "B" against biasing spring 198 translates such pivotal movement to longitudinal proximal movement of control members 50, 58 as indicated by arrow "L". Proximal movement of control member 58 and camming pin 130, which is movable therewith, approximates jaw assemblies 28 and 30 by camming interaction with camming slots 126a, 126b as described above.

Articulation Mechanism

Referring to FIG. 4, there is shown preferred mechanism for effectuating the articulation of distal jaw sections 36 and 38 relative to proximal jaw portions 32 and 34. The mechanism includes articulation rotating knob 40 which has a fluted outer surface to facilitate gripping by the user. The knob is provided with a stepped bore 94 having internal threading 96 on a portion thereof for engagement with corresponding threading on articulation screw 102. Knob 40 is mounted for rotational movement and is restrained against longitudinal movement by outer housing 24 at a proximal portion and at a distal portion by retainer 98 and shim 100. Shim 100 can be precisely machined at the time of assembly of the surgical apparatus 10 to insure a close tolerance with the distal portion of knob 40.

External threaded portion 104 on an outer surface of articulation screw 102 (FIG. 9) is configured to engage internal threading 96 of articulation knob 40 in order to transfer rotational motion of knob 40 to longitudinal displacement of articulation screw 102. Articulation screw 102 has a longitudinal bore and is dimensioned to be concentrically slidable over distal control member 58. FIG. 4 illustrates the location of a pair of stop plates 106a, 106b provided at the end portions of articulation screw 102. Stop plates 106a, 106b restrict the longitudinal displacement of articulation screw 102, and consequently the articulation of distal jaw portions 36, 38. In the preferred embodiment, both stop plates 106a, 106b and the proximal and distal faces 95, 97 of the internal treaded portion 96 are provided with a plurality of radially aligned, longitudinally extending projections 108 which intermesh when screw 102 reaches the preset limits of longitudinal displacement, thereby preventing further rotation of knob 40. FIG. 4 illustrates articulation screw 102 at its distal limit of travel, wherein proximal face 97 of knob 40 abuts stop plate 106b. The distal portion of articulation screw 102 is connected to 10 articulation tube 110 and bushing 174 which, in turn, are operatively connected with assemblies 28, 30.

In the portion of the description which follows, articulation will be described with regard to right jaw assembly 28, including distal jaw portion 36 and proximal jaw portion 32 only, although the mounting and articulation of left jaw assembly 30 occurs simultaneously in a substantially identical manner.

With initial reference to FIG. 6, proximal jaw portion 32 includes a clevis portion 124 having spaced apart shackles 134a, 134b defining a recess 137 for receiving the mounting portion 158 of distal jaw portion 36. Apertures 142a, 142b extend through shackles 134a, 134b. Mounting portion 158 of distal jaw portion 36 is provided with a first aperture 162 which corresponds with apertures 142a, 142b in shackles 134a, 134b of proximal jaw portion 32 for receiving barrel pin 146a. Articulation of distal jaw portion 36 with respect to proximal jaw portion 32 occurs about barrel pin 146a (See, FIG. 14).

Figure 17:
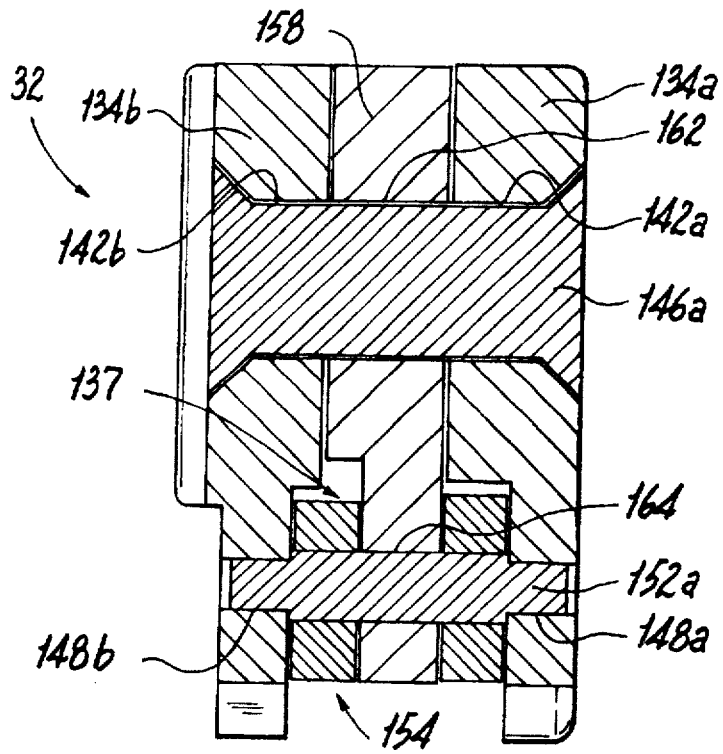
FIG. 17 is a cross-sectional view illustrating the distal and proximal jaw portions of the right jaw assembly, taken along line 17—17 of FIG. 15 passing through the pivot pin and the articulation linkage pin.

With continued reference to FIG. 6, articulation of jaw assembly 28 occurs by movement of an actuation mechanism including cylindrical bushing 174, articulation wire 180, and actuating legs or linkage members 154, 156. As illustrated in FIG. 17, recess 137 in proximal jaw portion 32 between shackles 134a, 134b is configured to receive mounting portion 158 including elongated linkage aperture 164 and a distal portion of a linkage member 154, which are pivotably linked by linkage pin 152a. A linkage aperture 164 in mounting portion 158 is offset from pivot aperture 162 such that longitudinal movement of linkage member 154 effects articulation of distal jaw portion 36. Elongated slots 148a, 148b extending through shackles 134a, 134b are configured to slidably receive linkage pin 152a to provide additional stability to the articulation mechanism. Linkage member 156 is similarly linked to distal jaw portion 30 by linkage pin 152b.

Referring back to FIG. 6, cylindrical bushing 174 is connected at the distal end of articulation tube 110 and is concentric with and surrounds distal control member 58 and is slidable within outer tube 22. Alternatively, the articulation screw 102, tube 110, and bushing 174 may be machined or formed in a single, integral piece. Bushing 174 transfers longitudinal movement of articulation screw 102 to the distal portion of the apparatus 10. Articulation wire 180 is connected to bushing 174 at one end and to respective linkage members 154 and 156 at the other end in order to effectuate the previously described longitudinal movement of linkage members 154 and 156.

FIGS. 14–15 illustrate the progressive articulation of distal jaw portion 36 with respect to proximal jaw portion 32 about pivot pin 146a. FIG. 14 illustrates linkage member 154 disposed in a proximal position adjacent proximal jaw portion 32. This corresponds to a non-articulated position of distal jaw portion 36. Referring now to FIG. 15, linkage member 154 has moved in a distal longitudinal direction as indicated by arrow "L", thereby pivoting distal jaw portion 36 in the direction of arrow "C". Linkage pin 152a travels longitudinally in slots 148a, 148b to stabilize and direct the movement of linkage member 154 within recess 137. (See, FIG. 17)

Figure 18:
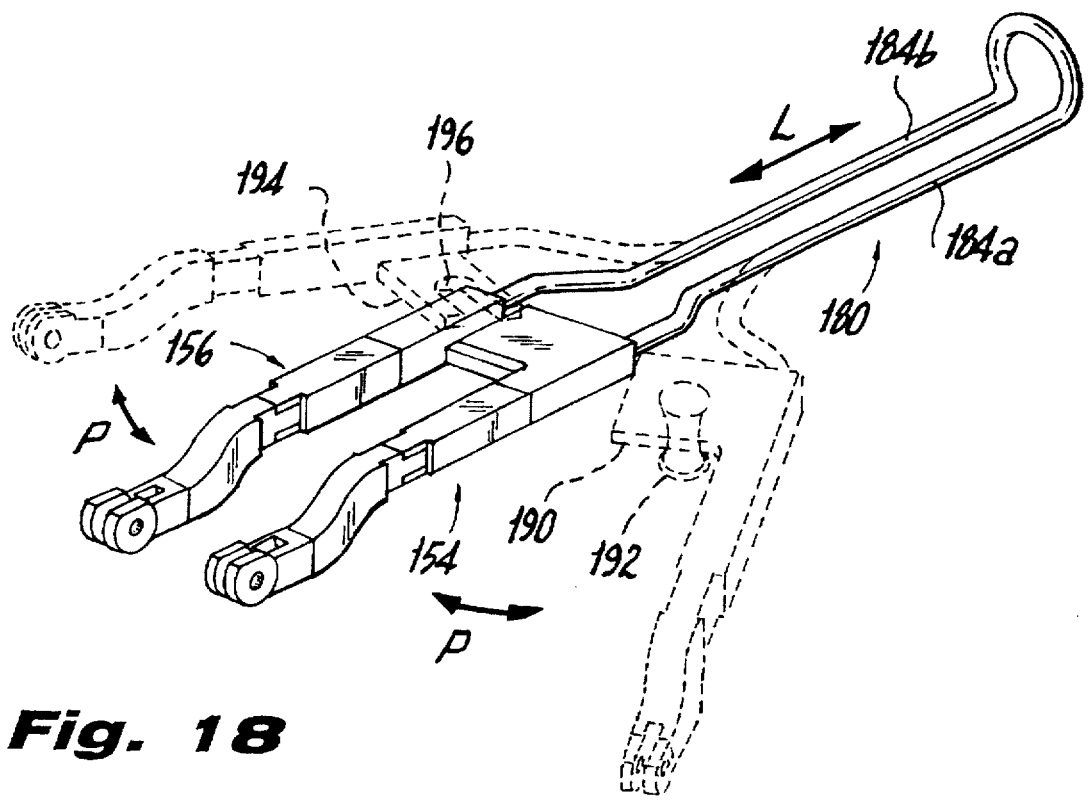
FIG. 18 is a perspective view of the articulation linkage members and the associated wire member illustrated in a closed position (the open position of the members indicated in phantom)

Turning to FIG. 18, articulation wire 180 is configured to be formed of stainless steel spring wire or a resilient shape memory alloy, the configuration of which can be controlled by applying a mechanical stress to the material. Consequently, linear sections 184a, 184b of articulation wire 180 are capable of bending as indicated in phantom. The connection of linkage members 154, 156 to proximal jaw portions 32, 34 by means of linkage pins 152a, 152b enables linkage members 154, 156 to move with proximal jaw sections 32, 34 as indicated by arrow "P" from a closed position indicated in solid line to an open position indicated in phantom. Linkage member 154 is provided with flange portion 190 having a pin 192 that cooperates with a channel 196 in flange portion 194 in linkage member 156. Pin 192 is slidable within channel 196 when proximal jaw sections are in a partially closed to fully closed position to prevent undesired asymmetrical articulation of one distal jaw portion with respect to the opposite side distal portion.

Rotation Mechanism

With reference to FIG. 2, surgical apparatus 10 includes a mechanism for rotating endoscopic portion 20 about its longitudinal axis relative to stationary handle portion 14 to increase the range of operability of the instrument. The elongated endoscopic portion 20 including outer housing 24 is rotatably mounted within the stepped bore 48 of barrel portion 18. Rotation knob 42 includes pin 41 disposed within notch 43 at the proximal end of outer housing 24 and operatively connects knob 42 to housing 24 so that upon rotation of knob 42, jaw assemblies 28 and 30 are rotatable therewith about the longitudinal axis. Handle sections 44, 46 are each provided with a longitudinally extending projection 112 and 114, respectively, engagable with a radial gearing (not shown) provided on a proximal face of rotation knob 42. Compression spring 118 biases the gearing of rotation knob 42 into engagement with projections 112 and 114 to facilitate indexed rotation of endoscopic portion 20 and jaw assemblies 28 and 30 in radially indexed movements.

Jaw Configuration

Referring now to FIGS. 19–22, there is shown one embodiment of the subject jaw assembly which takes on the form of a conventional Fogarty clamp in a fully deployed orientation. The distal jaw portion 238 includes a body portion 260 having a generally elongated configuration with a partially curved portion 240 adjacent the mounting portion 258 thereof. Two rows of interdigitating teeth 270 and 272 are formed along the length of distal jaw portion 238, with one row being disposed adjacent each peripheral edge of the jaw. As best seen in FIG. 20, channel 274 extends between rows 270 and 272 along a medial portion of the jaw to receive tissue gripped by the rows of teeth. The curvature of the jaw enables the surgeon to reach and clamp blood vessels and other structures without interfering with neighboring tissue. As indicated in FIG. 22, two rows of interdigitating teeth 276 and 278 can be formed on proximal jaw portion 232 extending from clevis portion 224 to intermediate portion 222. Channel 280 extends therebetween, and is interrupted at aperture 242a. When proximal jaw portion 232 and distal jaw portion 238 are pivotably linked by a barrel pin 146a (See, FIG. 6) inserted through apertures 262a and 242a, the rows of interdigitating teeth 270, 272, and 276, 278 form a continuous contact surface extending along the distal portion 238 and proximal portion 232.

Referring to FIG. 20, the cooperating distal jaw sections 236 and 238 are substantially identical, although mirror images of one another. Thus, the rows of interdigitating teeth on each jaw engage one another and a cavity is formed by the interposition of channel 274 for the reception of tissue gripped by teeth 270, 272 and 276, 278.

Turning now to FIGS. 23—26, there is shown another embodiment of the subject jaw assembly which takes the form of an Aortic Clamp in a fully deployed orientation. FIG. 23 illustrates distal jaw section 338 having a body portion 360 with a substantially constant radius of curvature "r". Two rows of interdigitating teeth 370 and 372 are provided on the edges along the length of distal jaw section 338. Distal jaw portion 338 cooperates with distal jaw portion 336. As depicted in FIG. 24-A, distal jaw portion 338 includes a recess or channel 374 extending along a substantial length of body portion 360. Between the two rows of interdigitating teeth 376 and 378 of distal jaw portion 336 is disposed a rib or projection 376 which extends along a substantial length of body portion 361 of distal jaw portion 336 and engages channel 374 of distal jaw section 338. The interaction of rib 376 within channel 374 compresses tissue structure such as blood vessels gripped between distal jaw sections 336 and 338. Transverse compression across a blood vessel would be useful to inhibit blood flow therethrough. FIG. 26 illustrates proximal jaw portion 332 having two rows of teeth 376 and 378 extending from the intermediate portion 322 to the clevis portion 324 and a channel 380 extending therebetween. Cooperating proximal jaw section (not shown) includes a channel to receive the rib or projection between the two rows of interdigitating teeth for interacting with channel 380 in proximal jaw section 332 to effectuate compression of vessels gripped therebetween. Clearly, the rib or projection can be formed on this proximal jaw section with the channel formed in the other proximal jaw section.

FIGS. 27–30 illustrate yet another embodiment of the present jaw assembly which takes the form of an Aortic Occlusion Clamp in the fully deployed position. FIG. 27 illustrates distal jaw portion 438 having body portion 460 with a non-linear configuration. Body portion 460 includes a proximal linear portion, a radiused intermediate portion and a distal linear portion. Extending along the length of body portion 460, in a medial portion, is a contact surface consisting of three adjacent rows of interdigitating teeth 472 having a staggered configuration. As illustrated in FIGS. 28-A and 28-B, teeth 472 of distal jaw portion 438 cooperate with teeth 474 of distal jaw portion 436 in order to grip and occlude vessels gripped therebetween. Referring to FIG. 30, clevis portion 424 and intermediate portion 422 of proximal jaw portion 432 are also provided with three rows of interdigitating teeth to provide a continuous contact surface across the proximal and distal jaw portions.

Operation of the Surgical Apparatus

In use, surgical apparatus 10 is normally prepared for insertion into the body cavity by placing jaw assemblies 28 and 30 in a closed position corresponding to pivoting handle 16 being in approximation with stationary handle 14 (See FIG. 8). Articulation knob 40 is rotated to position jaw assemblies 28 and 30 in a non-articulated or substantially straight configuration (See, FIGS. 1 and 14). Surgical apparatus 10 can be inserted in the body cavity either through a cannula or a small incision.

Once inside the body cavity, jaw assemblies 28 and 30 may be remotely manipulated at handle assembly 12 as surgical conditions require. In particular, trigger 92 is depressed to disengage pawl 88 from engagement with rack 84. By maintaining pressure on trigger 92, pivoting handle 16 may be opened, thereby camming jaw assemblies 28 and 30 to an opened position. Turning rotation knob 42 in incremental movements is performed to rotate jaw assemblies to the desired angular orientation near a blood vessel or tissue structure. Progressive articulation of jaw assemblies 28 and 30 to their deployed configuration (See, FIG. 15) is effectuated by rotation of articulation knob 40. Subsequent to positioning of jaw assemblies 28 and 30 about the tissue to be grasped, closure of the jaws is achieved by approximating the pivoting handle 16 with the stationary handle 14. The user will detect either audibly or in a tactile sense the progressive engagement of pawl 88 with rack 84. If closing force is removed from the handle portion, i.e. the surgeon releases handle assembly 12, then rack 84 and pawl 88 acting in conjunction with return spring 198 will maintain the selected closure of the jaw assemblies. The foregoing sequence of opening the jaw assembly, rotation, articulation and closure is described as illustrative only, since such functions of apparatus 10 may be performed in any order that surgical conditions may require. Removal of surgical apparatus 10 from the operative site is normally achieved by closing jaw assemblies 28 and 30 and returning them to the non-articulated or straightened configuration.

It will be understood that various modifications may be made to the embodiments disclosed herein. For example, the jaw assemblies may be provided with different profiles and tooth configurations. Therefore, the above description should not be construed as limiting, but merely as exemplifications of preferred embodiments. Those skilled in the art will envision other modifications within the scope and spirit of the claims appended hereto.

What is claimed is:

1. A surgical apparatus comprising:
   a) a handle portion;
   b) an elongated body portion extending distally from the handle portion and defining a longitudinal axis;
   c) a tool assembly operatively associated with a distal end portion of the body portion and including:
      i) a first jaw assembly having a proximal jaw portion and a distal jaw portion; and
      ii) a second jaw assembly having a proximal jaw portion and a distal jaw portion, the distal and proximal jaw portions of each jaw assembly being pivotably connected to one another and movable between first and second articulated positions;
   d) a jaw actuation mechanism including a resiliently bendable actuation member having first and second cooperating actuating legs, each leg being connected to a respective one of first and second linkage members, each linkage member extending at least partially through a respective one of the proximal jaw portions of the first and second jaw assemblies and each linkage member being connected to a respective distal jaw portion of the first and second jaw assemblies to effectuate simultaneous pivotable movement of the distal jaw portions relative to the proximal jaw portions of the tool assembly, wherein the distal jaw portions of the first and second jaw assemblies each have an elongated aperture through which a connecting member is disposed to attach the distal jaw portion to the respective linkage member movement of each said linkage member relative to a respective proximal jaw portion causing each said connecting member to slide along a respective elongated aperture; and
   e) a jaw control mechanism operatively connecting the handle portion and the tool assembly and configured to effect movement of the tool assembly between an open position and a closed position.

2. A surgical apparatus as recited in claim 1, wherein at least a portion of each actuating leg of the jaw actuation mechanism is disposed within a recess in the distal jaw portion.

3. A surgical apparatus as recited in claim 2, wherein each of the cooperating actuating legs is mounted for reciprocal movement along a respective longitudinal axis of each jaw assembly.

4. A surgical apparatus as recited in claim 3, wherein the proximal jaw portion of each jaw assembly has a slot formed on a distal section thereof for slidably receiving a pivot pin which connects an actuation leg to the distal jaw portion of the jaw assembly.

5. A surgical apparatus as recited in claim 1, wherein the actuation mechanism includes an elongated actuation shaft extending between the tool assembly and the handle portion and connected to the actuation member at a proximal end portion thereof.

6. A surgical apparatus as recited in claim 5, wherein the jaw actuation mechanism further includes a first rotating actuation knob for effecting axial rotation of the elongated body portion and a second rotating actuation knob operatively associated with a proximal end portion of the actuation shaft for effecting longitudinal movement of the actuation shaft and the actuation member.

7. A surgical apparatus as recited in claim 1, wherein the jaw control mechanism includes an elongated control shaft extending from a control handle pivotably associated with the handle portion to the tool assembly.

8. A surgical apparatus as recited in claim 7, wherein the jaw control mechanism includes a camming assembly at a distal end portion of the elongated control shaft, the camming assembly including a cam pin and an angled cam slot in each of the proximal jaw portions, the cam pin mounted for movement with respect to the cam slots to effectuate movement of the tool assembly between the open and closed positions.

9. A surgical apparatus as recited in claim 1, wherein the distal jaw portion has a partially curved configuration.

10. A surgical apparatus as recited in claim 9, wherein the distal jaw portion has a constant radius of curvature along the arc length thereof.

11. A surgical apparatus as recited in claim 9, wherein a major section of the distal jaw section is generally elongate in configuration.

12. A surgical apparatus as recited in claim 1, wherein the actuation member is bifurcated to form the first and second actuating legs, and each leg is movable between a longitudinally oriented first position and an angled second position wherein the first and second actuating legs are resiliently biased to the first longitudinally oriented first position.

13. A surgical apparatus as recited in claim 1, wherein the jaw actuation mechanism effects progressive pivotable movement of the distal jaw portions.

14. A surgical apparatus comprising:
 a) a handle portion;
 b) an elongated body portion extending distally from the handle portion and defining a longitudinal axis;
 c) a tool assembly operatively associated with a distal end portion of the body portion and including:
  i) a first jaw assembly having a proximal jaw portion and a distal jaw portion; and
  ii) a second jaw assembly having a proximal jaw portion and a distal jaw portion, the distal and proximal jaw portions of each jaw assembly defining a continuous contact surface and being pivotably connected to one another and movable between first and second positions;
 d) a jaw actuation mechanism connected to the first and second jaw assemblies to articulate the distal jaw portions with respect to the proximal jaw portions, wherein the jaw actuation mechanism includes a resiliently bendable longitudinally movable bifurcated actuation member of single piece construction having first and second cooperating actuating legs extending distally from a connecting portion, and wherein each distal jaw portion includes an elongated aperture through which a connecting member is disposed to pivotally attach the distal jaw portions to the jaw actuation mechanism movement of said jaw actuation mechanism relative to each of said proximal jaw portions causing each said connecting member to slide along a respective elongated aperture; and
 e) a jaw control mechanism operatively connecting the handle portion and the tool assembly and configured to effectuate movement of the tool assembly between an open position and a closed position; and
 f) an axially rotatable first actuation knob for effecting axial rotation of the elongated body portion.

15. A surgical apparatus as recited in claim 14, wherein the jaw actuation mechanism includes first and second linkage members each having a proximal end portion attached to a respective one of the first and second cooperating actuation legs and a distal end portion pivotally connected to a respective one of the distal jaw portions by means of the connecting member disposed through the respective elongated aperture, each linkage member extending at least partially through a respective one of the proximal jaw portions of the first and second jaw assemblies such that upon longitudinal translation of the bifurcated actuation member the distal jaw portions articulate with respect to the proximal jaw portions.

16. A surgical apparatus as recited in claim 14, wherein the proximal jaw portion of each jaw assembly has a slot formed on a distal section thereof for slidably receiving a pivot pin which connects an actuation leg to the distal jaw portion of the jaw assembly.

17. A surgical apparatus as recited in claim 14, wherein the jaw actuation mechanism includes an elongated actuation shaft which extends from the handle portion to the bifurcated actuation member.

18. A surgical apparatus as recited in claim 17, wherein the jaw actuation mechanism further includes an axially rotatable second actuation knob operatively associated with the handle portion for effectuating longitudinal movement of the actuation shaft.

19. A surgical apparatus as recited in claim 18, wherein the jaw control mechanism includes an elongated control shaft extending from a control handle pivotably associated with the handle portion to the tool assembly.

20. A surgical apparatus as recited in claim 14, wherein the control mechanism includes a camming assembly at a distal end portion of the elongated control shaft, the camming assembly including a cam pin and an angled cam slot in each of the proximal jaw portions, the cam pin mounted for movement with respect to the cam slots to effectuate movement of the jaw assembly between the open and closed positions.

21. A surgical apparatus as recited in claim 14, wherein the distal jaw portion has a partially curved configuration.

22. A surgical apparatus as recited in claim 21, wherein the distal jaw portion has a constant radius of curvature along the arc length thereof.

23. A surgical apparatus as recited in claim 21, wherein a major section of the distal jaw section is generally elongate in configuration.

24. A surgical apparatus comprising:
 a) a handle portion including a pivoting control handle;
 b) an elongated body portion extending distally from the handle portion and defining a longitudinal axis;
 c) a tool assembly operatively associated with a distal end portion of the body portion and including
  i) a first jaw assembly having a proximal jaw portion and a distal jaw portion,
  ii) a second jaw assembly having a proximal jaw portion and a distal jaw portion, the distal and proximal jaw portions of each jaw assembly being pivotably connected to one another and movable between first and second positions;

d) a jaw actuation mechanism connected to the first and second jaw assemblies to effectuate progressive pivotable movement of the distal jaw portions relative to the proximal jaw portions. wherein the jaw actuation mechanism includes an actuation member having first and second cooperating legs. each leg being connected to a respective one of first and second links. each link extending at least partially through a passageway in a respective one of each of the proximal jaw portions of the first and second jaw assemblies. wherein the distal jaw portions of the first and second jaw assemblies each have an elongated aperture through which a respective connecting member is laterally disposed to attach the distal jaw portions to a respective one of the first and second links movement of each said link relative to a respective proximal jaw portion causing each said connecting member to slide along a respective elongated aperture;

e) a jaw control mechanism operatively connecting the pivoting control handle and the tool assembly to effectuate movement of the first and second jaw assemblies between an open position and a closed position; and f) a first rotation mechanism operatively connected to the tool assembly and associated with the handle portion to effectuate angular rotation of the tool assembly around the longitudinal axis.

25. A surgical apparatus as recited in claim 24. wherein the actuation member is constructed as a single piece from resiliently bendable material.

26. A surgical apparatus as recited in claim 24. wherein the jaw actuation mechanism further includes a rotating actuation knob operatively associated with a proximal end portion of an actuation shaft for effectuating longitudinal movement of the actuation shaft and actuation member.

27. A surgical apparatus as recited in claim 26. wherein the distal and proximal jaw portions of each jaw assembly define a continuous contact surface.

28. A surgical apparatus as recited in claim 26. wherein the actuation member has first and second cooperating actuating legs. each leg being operatively connected to a respective distal jaw portion of the first and second jaw assemblies.

29. A surgical apparatus as recited in claim 24 further including a pawl and rack mechanism operatively associated with the jaw control mechanism for releasably maintaining selected incremental closure configurations of the first and second jaw assemblies. the pawl being operatively connected to a release trigger.

* * * * *